United States Patent [19]

Bugge

[11] Patent Number: 5,025,779
[45] Date of Patent: Jun. 25, 1991

[54] DEVICE INTENDED TO BE USED FOR OPENING THE CHEST DURING SURGERY

[76] Inventor: Mogens Bugge, Sövdeborgsgatan 64, 216 20 Malmö, Sweden

[21] Appl. No.: 395,029

[22] Filed: Aug. 16, 1989

[30] Foreign Application Priority Data

Aug. 16, 1988 [SE] Sweden ............................... 8802904

[51] Int. Cl.⁵ .............................................. A61B 17/02
[52] U.S. Cl. ...................................................... 128/20
[58] Field of Search .......................... 128/17, 18, 20; 269/328

[56] References Cited

U.S. PATENT DOCUMENTS

| 4,049,000 | 9/1977 | Williams | 128/20 |
| 4,151,838 | 5/1975 | Crew | 128/20 |
| 4,627,421 | 12/1986 | Symbas et al. | 128/20 |
| 4,726,356 | 2/1988 | Santilli et al. | 128/20 |
| 4,747,395 | 5/1988 | Brief | 128/20 |
| 4,829,985 | 5/1989 | Couetil | 128/20 |
| 4,852,552 | 8/1989 | Chaux | 128/20 |
| 4,865,019 | 9/1989 | Phillips | 128/20 |
| 4,884,559 | 12/1989 | Collins | 128/17 |

FOREIGN PATENT DOCUMENTS

| 0246086 | 11/1987 | European Pat. Off. | |
| 1055-497-A | 7/1988 | U.S.S.R. | |
| 1360-706-A | 7/1988 | U.S.S.R. | |
| 168216 | 9/1921 | United Kingdom | 128/20 |

Primary Examiner—Edward M. Coven
Assistant Examiner—Mark S. Graham
Attorney, Agent, or Firm—Ostrolenk, Faber Gerb & Soffen

[57] ABSTRACT

A device intended to be used for opening of the chest during heart operations or other surgical procedures, said device comprising a pair of substantially opposed hook-provided (3,4) plates (1,2) intended to grip about opposite incision edges of the operations incision, said hook-provided plates (1,2) are interconnected by a frame structure (6) or the like, which is provided with first adjusting members (7) for adjusting the relative distance between the hook-provided plates (1,2). At least one hook-provided plate, (1) is via a hinge (8), arranged substantially parallel with the gripping direction of the respective hook-provided plate connected to a member (9) provided with an adjusting screw (10), which is arranged to act upon said hook-provided plate (1) to tilt this about the hinge (8) and lift the respective incision edge away from the underlying body tissues. Thus an asymmetric opening of the chest is achieved.

8 Claims, 2 Drawing Sheets

DEVICE INTENDED TO BE USED FOR OPENING THE CHEST DURING SURGERY

TECHNICAL FIELD

The present invention refers to a device intended to be used for opening of the chest during heart operations or other surgical procedures, said device comprising a pair of substantially opposed hook-provided means intended to grip about opposite incision edges of the operation incision, said hook-provided means are interconnected by a frame structure or the like, which is provided with first adjusting members for adjusting the relative distance between the hook-provided means.

BACKGROUND OF THE INVENTION

Heart surgery is usually performed through an incision in the midline of the chest (median sternotomy) which gives a fair access to the heart and to other organs within the thoracic cavity. However, at coronary by-pass surgery which is becoming a routine operation in industrialized countries, there is a need for opening the chest in an asymmetric way since at this operation one may very often use the internal mammary artery which is an artery running longitudinally along the interior surface of the sternum. In order to dissect this artery, the surgeon must see the inside of the sternum and therefore an asymmetric opening of the thoracic cavity is necessary.

Several retractors for opening the chest in a symmetric way exist and even a few for asymmetric opening have been presented so far. The latter, however, have so far been complicated, expensive and have not opened the chest sufficiently.

SUMMARY OF THE INVENTION

The object of the present invention is to provide a device of the kind mentioned above, which is designed to open the chest in an asymmetric way, which has a simple construction and is simple to handle, to clean and to sterilize. This has according to the invention been provided by the fact that at least one hook-provided means via a hinge arranged substantially parallel with the gripping direction of the respective hook-provided means, is connected to a member provided with a second adjusting means, which is arranged to act upon said hook-provided means to tilt this about the hinge and lift the respective incision edge away from the underlying body tissues.

DESCRIPTION OF THE PREFERRED EMBODIMENTS

Figure 1:
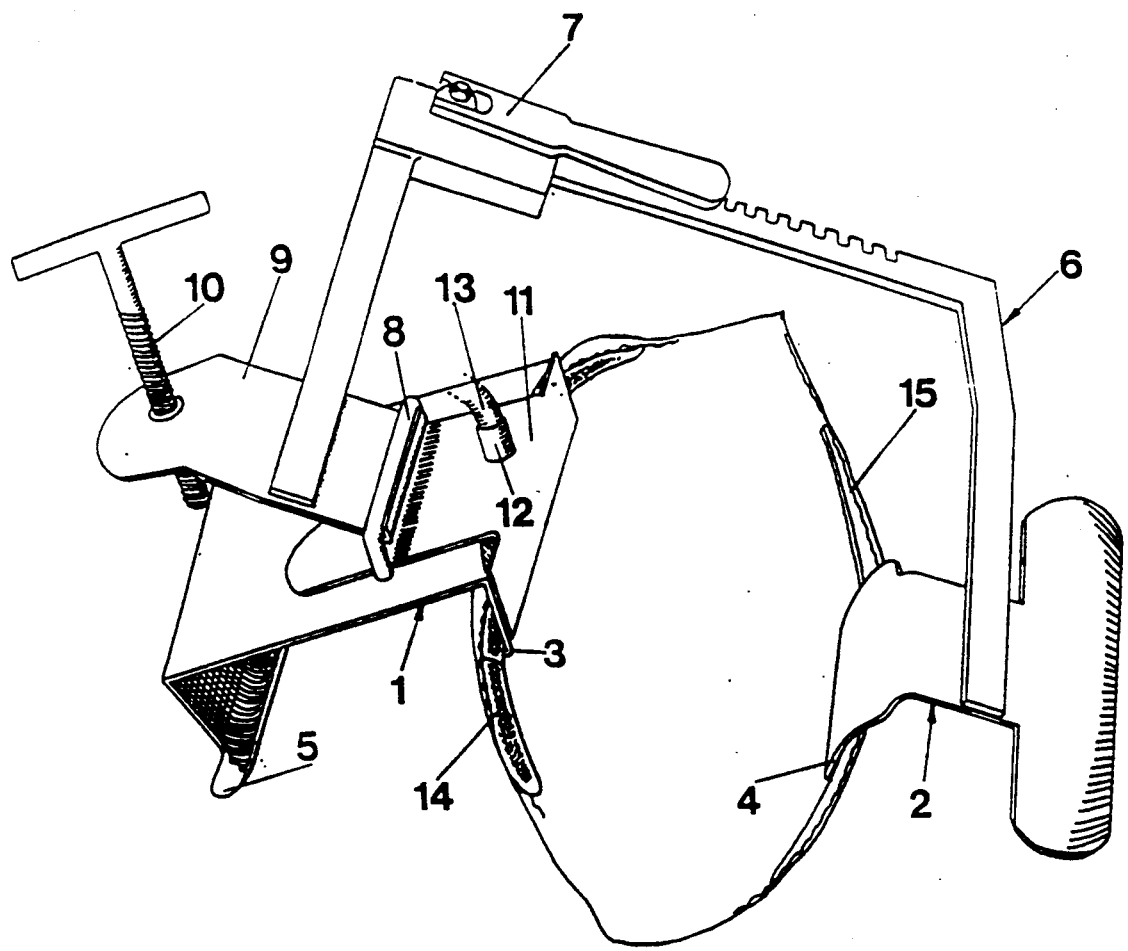
FIG. 1 is a perspective of a preferred embodiment of the device of the present invention.

The device comprises two plates 1 and 2 provided with hook-shaped members 3 and 4 resp. The first plate 1 is provided with a downward support 5 at the end remote from the hook 3. The hook-provided plates 1 and 2 are connected to each other via a frame structure 6 provided with adjusting means 7 for adjusting the distance between the plates 1 and 2 and by that the hooks 3 and 4.

The first hook-provided plate 1 is via a hinge 8 connected to a lever arm 9, which at the end remote from the hinge 8 is provided with an adjusting screw 10 arranged to act upon the plate 1 for tilting it about the hinge 8.

An angle plate 11 is further arranged on the hook-provided plate 1 outside the hook-shaped portion 3 thereof. The plate 11 has connection means 12 for a suction hose 13 for suction of foam produced from diatherma within the thoriacic cavity. The plate 11 is guided so that its downward portion can be displaced a distance from the hook 3, so that a gap is formed therebetween.

Figure 2:
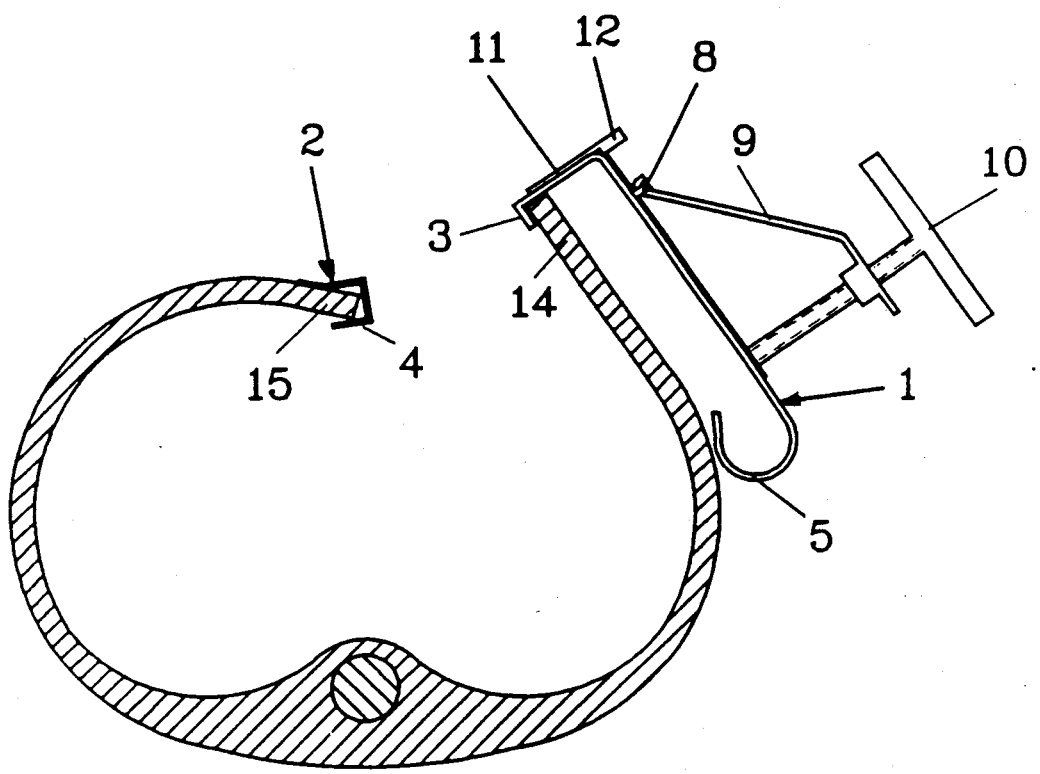
FIG. 2 is a cross-section through the device of FIG. 1.

The device is used in the following way. After median sternotomy the device is applied with its hooks 3 and 4 gripping about the opposite sternum halves 12 and 13 as is shown in FIG. 1. The thoriacic cavity is spread apart by pulling the plates 1 and 2 with the hooks 3 and 4 apart by means of the adjusting means 7. When the two sternum halves have been brought apart the desired distance one turns the adjusting screw 10, which acts upon the plate 1 and tilts this about this hinge 8, so that the hook-provided portion is lifted. The sternum of the side in question is then lifted, which is seen from FIG. 2 so that arteria mammaria will be accessible for dissection.

The device is preferably manufactured by stainless steel or other metal alloy or a material which withstands the stresses and loads in question. No special service instruments are needed. It is easy to clean and sterilize and has been constructed on order to be safe and easy to handle by the surgeon and by the staff.

Even if the main field of application will be at dissection of arteria mammaria in coronary surgery other applications are also possible, e.g. in connection with surgical operations of tumours in the chest, which sometimes can be difficult to dissect through a symmetric opening.

The invention is of course not limited to the embodiment shown, but a plurality of variants are possible within the scope of the claims.

I claim:

1. A refractor for opening the chest during surgery, said retractor comprising:
   first and second substantially opposed retractor blades with first and second hooks, respectively, for gripping opposite incision edges of a chest incision, the first and second retractor blades being spaced and mounted to extend substantially parallel to each other in all positions thereof;
   a frame structure, said retractor blades being interconnected by said frame structure;
   a first adjusting means associated with the frame structure for adjusting the relative distance between the first and second blades; and
   a second adjusting means arranged to act upon the first retractor blade to tilt the first retractor blade in a manner which enables lifting of the first hook and the incision edge gripped by it upwards while maintaining the first and second retractor blades oriented substantially parallel to each other.

2. The retractor of claim 1, wherein said second adjusting means comprises a hinged arranged substantially parallel with a gripping direction of the first hook, said first retractor blade being pivotable about said hinge.

3. The retractor of claim 2, wherein said second adjusting means further comprises a lever arm, one end of said lever arm comprising said hinge and an opposite end of said lever arm comprising means for adjusting said lever arm.

4. The retractor of claim 3, wherein said lever arm adjusting means comprises a screw.

5. The retractor of claim 1, further comprising suction means for providing suction at at least one of said retractor blades.

6. The retractor of claim 5, wherein said suction means comprises a plate disposed at said at least one retractor blade and a connection means for a suction hose disposed at said plate.

7. The retractor of claim 4 further comprising suction means for providing suction at at least one of said retractor blades.

8. The retractor of claim 7, wherein said suction means comprises a plate disposed at said at least one retractor blade and a connection means for a suction hose disposed at said plate.

* * * * *